(12) United States Patent
Shan et al.

(10) Patent No.: US 10,513,480 B2
(45) Date of Patent: Dec. 24, 2019

(54) OXIDATIVE CONVERSION OF METHANE TO OXYGENATES

(71) Applicant: Trustees of Tufts College, Medford, MA (US)

(72) Inventors: Junjun Shan, Medford, MA (US); Maria Flytzani-Stephanopoulos, Winchester, MA (US); Mengwei Li, Medford, MA (US)

(73) Assignee: Trustees of Tufts College, Medford, MA (US)

( * ) Notice: Subject to any disclaimer, the term of this patent is extended or adjusted under 35 U.S.C. 154(b) by 0 days.

(21) Appl. No.: 15/774,862

(22) PCT Filed: Nov. 9, 2016

(86) PCT No.: PCT/US2016/061064
§ 371 (c)(1),
(2) Date: May 9, 2018

(87) PCT Pub. No.: WO2017/083338
PCT Pub. Date: May 18, 2017

(65) Prior Publication Data
US 2018/0319728 A1   Nov. 8, 2018

Related U.S. Application Data

(60) Provisional application No. 62/253,327, filed on Nov. 10, 2015.

(51) Int. Cl.
| | | |
|---|---|---|
| C07C 29/50 | (2006.01) | |
| C07C 51/215 | (2006.01) | |
| B01J 29/04 | (2006.01) | |
| B01J 29/06 | (2006.01) | |
| B01J 29/44 | (2006.01) | |
| B01J 29/46 | (2006.01) | |
| B01J 35/00 | (2006.01) | |
| B01J 23/46 | (2006.01) | |

(52) U.S. Cl.
CPC ............. *C07C 29/50* (2013.01); *B01J 23/464* (2013.01); *B01J 29/04* (2013.01); *B01J 29/06* (2013.01); *B01J 29/44* (2013.01); *B01J 29/46* (2013.01); *B01J 35/002* (2013.01); *C07C 51/215* (2013.01); *B01J 2229/18* (2013.01); *Y02P 20/52* (2015.11)

(58) Field of Classification Search
CPC . B01J 23/464; B01J 29/44; B01J 29/46; B01J 35/002; B01J 2229/18; C07C 29/50; C07C 51/215
See application file for complete search history.

(56) References Cited

U.S. PATENT DOCUMENTS 5,393,922 A    2/1995  Sen et al.
2013/0324761 A1  12/2013  Hutchings et al.

FOREIGN PATENT DOCUMENTS

WO    WO2011060917    *   2/2011

OTHER PUBLICATIONS

English translation of WO2011060917, pp. 1-22. (Year: 2011).*
Forde "Low Temperature Aqueous Phase Oxidation of Alkanes with Metal Oped Zeolites Prepared by Chemical Vapour Infiltration" Ph.D. Dissertation, Cardiff University, 2011.
Hammond et al "Direct Catalytic Conversion of Methane to Methanol in an Aqueous Medium by Using Copper-Promoted Fe-ZSM-5" Angewandte Chemie vol. 124, pp. 1-6, 2012.
Li et al "Direct Catalytic Conversion of Methane to Methanol and Acetic Acid Using Molecular Oxygen in an Aqueous Medium Over RH/ZSM-5 and IR/ZSM-5" Proceedings of ISCRE 24, Foundations and Vistas of Chemical Reaction Engineering, 2016.
Palkovits et al "Solid Catalysts for the Selective Low-Temperature Oxidation of Methane to Methanol" Angewandte Chemie vol. 48, pp. 6909-6912, 2009.
Shan et al "Catalytic Conversion of Methane to Methanol and Acetic Acid on Single-Site Metal Catalysts Under Mild Conditions" Proceedings of 2015 AlchE Annual Meeting, Salt Lake City, 2015.
Xu et al "Continuous Selective Oxidation of Methane to Methanol over Cu- and Fe-Modified ZSM-5 Catalysts in a Flow Reactor" Catalysis Today vol. 270, pp. 93-100, 2015.

* cited by examiner

*Primary Examiner* — Yate' K Cutliff
(74) *Attorney, Agent, or Firm* — Cesari and McKenna, LLP

(57) ABSTRACT

A method of converting methane to an oxygenate. The method includes converting methane to an oxygenate with a transition metal ion loaded zeolite catalyst in an aqueous medium in the presence of gaseous $O_2$ and CO at a temperature lower than 200° C. Also disclosed are a two-metal ion zeolite catalyst for converting methane to methanol and a method for preparing the two-metal ion zeolite catalyst.

22 Claims, No Drawings

OXIDATIVE CONVERSION OF METHANE TO OXYGENATES

CROSS-REFERENCE TO RELATED APPLICATIONS

This application is the National Stage of International Application No. PCT/US2016/061064, filed Nov. 9, 2016, which claims the benefit of Provisional Application No. 62/253,327, filed Nov. 10, 2015. The contents of both applications are hereby incorporated by reference in their entirety.

GOVERNMENT SUPPORT

This invention was made with government support under grant DE-AR0000433 awarded by the Department of Energy. The government has certain rights in the invention.

BACKGROUND

Methane, an abundant energy resource, is the main component of natural gas, which is largely produced from shale-gas formations. Conversion of methane to oxygenates, e.g., methanol and acetic acid, is of great importance. Indeed, it has attracted much attention, given broad applications of oxygenates in the chemical field.

Most current processes indirectly convert methane to methanol or acetic acid, which require multiple steps. For example, methane is converted to methanol through a two-step process (i.e., steam reforming methane to syngas and then transforming the syngas to methanol) and methane is converted to acetic acid via a three-step process (i.e., steam reforming methane to syngas, transforming the syngas to methanol, and finally converting the methanol to acetic acid).

Direct conversion of methane to methanol or acetic acid is becoming more popular than the current processes. Yet, there are three major disadvantages associated with current direct conversion of methane to methanol or acetic acid: use of an expensive oxidant, e.g., $H_2O_2$, low yield, and poor selectivity.

There is a need for a new method that directly converts methane to methanol or acetic acid, employs an inexpensive oxidant, and affords high yields and selectivity.

SUMMARY

This invention relates to a method for direct conversion of methane to methanol or acetic acid. The method uses easily accessible gaseous $O_2$ as the oxidant, and affords unexpectedly both high yields and high selectivity.

In one aspect, the present invention is a method of converting methane to oxygenates, e.g., methanol and acetic acid. The method includes the following steps: (1) providing a transition metal ion loaded zeolite catalyst, (2) converting methane to an oxygenate with the catalyst in an aqueous medium in the presence of gaseous $O_2$ and CO at a temperature lower than 200° C., and (3) collecting the oxygenate thus formed. The catalyst used in this method is a rhodium zeolite catalyst, a copper zeolite catalyst, an iron zeolite catalyst, a nickel zeolite catalyst, an iridium zeolite catalyst, or a combination thereof. The oxygenate, in liquid form, contains both methanol and acetic acid, in which the content of the methanol, the acetic acid, or the methanol and the acetic acid combined is greater than 50 mol %.

In another aspect, this invention is a method for converting methane to methanol. The method include the following steps: (1) providing a transition metal ion loaded catalyst, (2) converting methane to methanol with the transition metal ion loaded catalyst in an aqueous medium in the presence of gaseous $O_2$ and CO at a temperature lower than 200° C., and (3) collecting the methanol thus formed, in which the transition metal ion loaded catalyst is a transition metal catalyst loaded on a metal oxide support or a transition metal zeolite catalyst.

The transition metal catalyst loaded on a metal oxide support can be a rhodium catalyst loaded on $TiO_2$.

Examples of the transition metal zeolite catalyst include, but are not limited to, a rhodium zeolite catalyst, a copper zeolite catalyst, an iron zeolite catalyst, a nickel zeolite catalyst, an iridium zeolite catalyst, and a two-metal ion zeolite catalyst.

A further aspect of this invention is a two-metal ion zeolite catalyst for converting methane to methanol, the catalyst containing two transition metals, e.g., Pd and Ir, Cu and Ir, Fe and Ir, Pd and Rh, Cu and Rh, or Ag and Rh.

Also within the scope of this invention is a method for preparing a two-metal ion zeolite catalyst that can be used for converting methane to methanol. The method includes the following steps: (1) forming a transition metal ion loaded zeolite catalyst, the catalyst containing one transition metal, (2) introducing another transition metal into the catalyst thus formed to obtain a two-metal ion zeolite catalyst, and (3) reducing the two-metal ion zeolite catalyst thus obtained in 5% $H_2$/He (i.e., 5% $H_2$ balanced in helium), in which the two-metal ion zeolite catalyst contains two transition metals, the two transition metals being Pd and Ir, Cu and Ir, Fe and Ir, Pd and Rh, Cu and Rh, or Ag and Rh.

The details of the invention are set forth in the description below. Other features, objects, and advantages of the invention will be apparent from the following detailed description of several embodiments, and also from the appending claims.

DETAILED DESCRIPTION

Disclosed in detail herein is a method for direct conversion of methane to oxygenates, e.g., methanol and acetic acid. A general protocol for the direct conversion of methane to oxygenates is set forth below.

A transition metal ion loaded zeolite catalyst is synthesized according to known methods, e.g., incipient wetness impregnation, excess solution impregnation, vapor deposition, and ion exchange. Methane is activated and subsequently converted to a liquid oxygenate product, henceforth termed "oxygenate" (i.e., methanol, acetic acid, or a liquid mixture containing both of them), by using the catalyst in an aqueous medium in the presence of gaseous $O_2$ and CO at a temperature lower than 200° C. The oxygenate thus formed is collected. The gaseous CO and any gaseous CO2 produced during the process are not counted in the oxygenate.

The oxygenate produced by this method contains methanol and acetic acid as the major liquid products. More specifically, the content of the methanol, the acetic acid, or both the methanol and the acetic acid combined in the oxygenate is greater than 50 mol %.

The transition metal ion loaded zeolite catalyst, i.e., a rhodium zeolite catalyst, a copper zeolite catalyst, an iron zeolite catalyst, a nickel zeolite catalyst, an iridium zeolite catalyst, or a combination thereof, generally has a transition metal loading of 0.1-1.0 wt % (e.g., 0.5 wt %). Of note, the transition metal ion loaded zeolite catalyst can contain one or more transition metals (e.g., one transition metal plus a non-transition metal, two transition metals, and three transition metals). Specific examples of the transition metal ion loaded zeolite catalyst include, but are not limited to, RhNa-ZSM-5, IrCu-ZSM-5, and IrCuPd-ZSM-5.

The transition metal ion loaded zeolite catalyst can be made from one or more transition metal salts and a zeolite. Examples of a transition metal salt include, but are not limited to, a rhodium salt, a copper salt, an iron salt, a nickel salt, an iridium salt, a palladium salt, and a silver salt. The zeolite can have a Si/Al ratio of 5-1000 (e.g., 15 and 100). Examples of the zeolite used for preparing the catalyst include, but are not limited to, Zeolite Socony Mobil-5 (ZSM-5), mordenite (MOR), Ferrierite, Faujacite, Chabacite, beta zeolite (BEA), Y zeolite, X zeolite, SSZ-13, titanium silicalite-1 (TS-1), Amicite, Barrerite, Clinoptilolite, Harmotome, Laumontite, Paulingite, Pollucite, and mesoporous silica (e.g., MCM41).

Typically, the transition metal ion loaded zeolite catalyst used in this method is a rhodium zeolite catalyst. An exemplary rhodium zeolite catalyst is a Rh-ZSM-5 or Rh-MOR catalyst. Either catalyst can be prepared by incipient wetness impregnation of a rhodium nitrate solution into $NH_4$-ZSM-5 or $NH_4$-MOR, followed by treatment in 5% $H_2$/He at 550° C. for a certain time (e.g., 3 hours). In one example, the Rh-ZSM-5 or Rh-MOR catalyst thus prepared has a Rh loading of 0.1-1.0 wt % (e.g., 0.5 wt %).

Referring to the protocol set forth above, the gaseous $O_2$ typically has a pressure of 0.5-4.0 bar (e.g., 1.0-2.0 bar) and the gaseous CO typically has a pressure of 5 bar or lower (e.g., 1.0 bar). The aqueous medium can be deionized water. Generally, conversion of the activated methane to an oxygenate is performed at a temperature higher than 110° C. (e.g., 130-170° C.).

Methane can be converted into acetic acid as the major oxygenate, e.g., more than 70% of the total oxygenates. In one study, the yield of the acetic acid was close to 5500 μmol/gcat.

Also within this invention is a method for converting methane to methanol. An illustrative protocol for converting methane to methanol is described below.

A transition metal ion loaded zeolite catalyst is synthesized according to methods well known in the field, e.g., incipient wetness impregnation. Methane is activated and subsequently converted to methanol at a temperature lower than 200° C. with the catalyst in an aqueous medium in the presence of gaseous $O_2$ and CO. The methanol thus formed is collected.

The transition metal ion loaded zeolite catalyst used in this method is a rhodium zeolite catalyst, a copper zeolite catalyst, an iron zeolite catalyst, a nickel zeolite catalyst, an iridium zeolite catalyst, or a two-metal ion zeolite catalyst; preferably, a copper zeolite catalyst, an iron zeolite catalyst, or a two-metal ion zeolite catalyst.

Generally, in the illustrative protocol just described above, the gaseous $O_2$ has a pressure of 0.5-4.0 bar (e.g., 1.0-2.0 bar), conversion of the activated methane to methanol is performed at a temperature higher than 110° C. and lower than 200° C. (e.g., 130-170° C.).

In one example, the copper zeolite catalyst or the iron zeolite catalyst is prepared by incipient wetness impregnation, followed by treatment in air at 550° C. and then reduction in 5% $H_2$/He at 550° C. The copper zeolite or iron zeolite catalyst has a copper or iron loading of 0.1-1.0 wt %.

In another example, the two-metal ion zeolite catalyst contains two transition metals. The two transition metals can be Pd and Ir, Cu and Ir, Fe and Ir, Pd and Rh, Cu and Rh, or Ag and Rh. Each of the transition metals, i.e., Pd, Cu, Fe, Ir, Ag, and Rh, typically has a metal loading of 0.1-1.0 wt % (e.g., 0.5 wt %). Preferably, the two transition metals are Cu and Ir, or Fe and Ir; and the two-metal ion zeolite catalyst has a Cu, Fe, or Ir loading of 0.1-1.0 wt %, and a Cu/Ir or Fe/Ir molar ratio of 1:1.

Sill within the scope of this invention is a two-metal ion zeolite catalyst for converting methane to methanol, the catalyst containing two transition metals that can be Pd and Ir, Cu and Ir, Fe and Ir, Pd and Rh, Cu and Rh, or Ag and Rh.

The two-metal ion zeolite catalyst typically has a Pd, Cu, Fe, Ir, Ag, or Rh loading of 0.1-1.0 wt % and a Pd/Ir, Cu/Ir, Fe/Ir, Pd/Rh, Cu/Rh, or Ag/Rh molar ratio of 1:1 to 1:10.

An exemplary two-metal ion zeolite catalyst contains two transition metals that are Cu and Ir, or Fe and Ir. It has a Cu, Fe, or Ir loading of 0.1-1.0 wt %; and a Cu/Ir or Fe/Ir molar ratio of 1:1.

Further covered by this invention is a method for preparing a two-metal ion zeolite catalyst that can be used for converting methane to methanol. Described below is a general procedure for making such a two-metal ion zeolite catalyst.

A transition metal ion loaded zeolite catalyst, containing a transition metal, is synthesized according to known methods, e.g., incipient wetness impregnation, excess solution impregnation, chemical vapor deposition, and ion exchange. Another transition metal is then introduced into the catalyst to obtain a two-metal ion zeolite catalyst. Finally, the two-metal ion zeolite catalyst thus obtained is reduced in 5% $H_2$/He at 550° C.

The two transition metals contained in the two-metal ion zeolite catalyst thus prepared are Pd and Ir, Cu and Ir, Fe and Ir, Pd and Rh, Cu and Rh, or Ag and Rh.

In one example, the two-metal ion zeolite catalyst thus prepared contains two transition metals of Pd and Ir and has a Pd/Ir molar ratio of 1:10.

In another example, the two-metal ion zeolite catalyst prepared by the just-described method contains two metals being Cu and Ir, or Fe and Ir, each of them having a metal loading of 0.1-1.0 wt % (e.g., 0.5 wt %); and the catalyst has a Cu/Ir or Fe/Ir molar ratio of 1:1.

To prepare a two-metal ion zeolite catalyst, one can initially synthesize a copper zeolite or iron zeolite catalyst and then introduce iridium into the catalyst thus formed to obtain a two-metal ion zeolite catalyst, i.e., IrCu-ZSM-5. The copper zeolite or iron zeolite catalyst can be prepared by incipient wetness impregnation, followed by calcination in air at 550° C.

Without further elaboration, it is believed that one skilled in the art can, based on the above description, utilize the present invention to its fullest extent. The following specific examples are, therefore, to be construed as merely illustrative, and not limitative of the remainder of the disclosure in any way whatsoever. All publications cited herein are incorporated by reference.

Example 1: Preparation of a Rh-ZSM-5 Catalyst and Characterization Thereof

Preparation of a Rh-ZSM-5 Catalyst

Zeolite $NH_4$-ZSM-5 with a Si/Al ratio of 15 was purchased from Alfa and used without any modifications. The zeolite was dried in a vacuum oven at 100° C. for 3 hours to remove residual water from the internal pores of it. Subsequently, Rh cations were introduced by incipient wetness impregnation of a rhodium nitrate solution (99%, Sigma-Aldrich) into the dehydrated NH4-ZSM-5. After the impregnation, the material thus obtained was dried in a vacuum oven at 60° C. overnight and reduced in 5% $H_2$ (balanced in helium) at 550° C. for 3 hours to provide a Rh-ZSM-5 catalyst.

Characterization of a Rh-ZSM-5 Catalyst

The Rh-ZSM-5 catalyst prepared above was characterized with X-ray Diffraction (XRD), Transmission Electron Microscopy (TEM), X-ray Photoelectron Spectroscopy (XPS), Diffuse Reflectance Infrared Fourier Transform Spectroscopy (DRIFTS), and Extended X-ray Absorption Fine Structure (EXAFS).

XRD patterns were collected on a PANalytical X'Pert Pro instrument using nickel-filtered CuKα radiation (λ=1.54056 Å). Measurements were taken at 45 kV and 40 mA in a continuous mode and 2θ range from 10° to 60°. Aberration-corrected high-angle annular dark-field (HAADF) STEM images of RhZSM-5 were obtained with a JEOL 2200FS-AC STEM/TEM system at Oak Ridge National Laboratory. The samples for TEM characterization were prepared by dropping their colloidal solutions onto copper grids supported on carbon films. EDS imaging was collected with a Bruker-AXS 30 mm² silicon-drift detector system, which was operated at 200 kV for all imaging and EDS work.

XPS data were collected in a PHI VersaProbe II system equipped with a monochromatic AlKα source and a double focusing hemispherical analyzer. The XPS system was equipped with an argon ion sputter gun to sputter the sample for the depth-profile analysis of the sample. XPS samples were prepared by loading the catalyst powder onto a Cu foil.

DRIFTS measurement was conducted on a Thermo Scientific Nicolet iS50 FTIR Spectrometer and a Praying Mantis high temperature reaction chamber. CO adsorption on various samples was performed at room temperature. Pure CO was introduced into the DRIFTS cell at a flow rate of 10 mL/min. After flowing with CO, a He purge at a flow rate of 20 mL/min was applied to remove gas phase CO in the cell prior to the DRIFTS measurement.

In-situ X-ray absorption spectroscopy (XAS) data were obtained at beamline 12-BM at Argonne National Laboratory. XAS data of the Rh-ZSM-5 catalyst as synthesized at the Rh K-edge in fluorescence mode were collected at room temperature. Approximately 5 consecutive scans were collected for each sample to improve the signal-to-noise ratio. EXAFS data processing and analysis were performed using the IFEFFIT package.

XRD patterns of the Rh-ZSM-5 catalyst, Rh-ZSM-5 catalyst after reaction for 1 hour, and Rh-ZSM-5 catalyst after reaction for 3 hours, as well as pure ZSM-5, were collected. The XRD patterns of as-synthesized Rh-ZSM-5 showed no observable difference as compared with pure ZSM-5, indicating that the impregnation of Rh did not change the lattice structure of ZSM-5. Moreover, the XRD patterns of Rh-ZSM-5 catalysts after a 1-hour reaction and a 3-hour reaction were preserved, suggesting that the methane oxidative conversion reaction did not alter the lattice structure of ZSM-5. In addition, the XRD patterns showed that no diffraction peaks related to Rh oxides or metallic Rh were present, indicating well dispersed Rh species.

Aberration-corrected HAADF/STEM images were obtained on a thin edge of the Rh-ZSM-5 flake thus obtained, in which the Rh atoms could be imaged. Of note, unlike Rh atoms on other supports, it is generally very challenging to image Rh atoms on the ZSM-5 support, as its structure is rapidly destroyed by the sub-Ångstrom scanning electron beam. Unexpectedly, it was observed that STEM images showed unambiguously the imaging of single Rh atoms. In other words, isolated mononuclear Rh species were clearly presented in the Rh-ZSM-5 catalysts.

EXAFS data of a Rh-ZSM-5 catalyst were collected at the Rh K-edge in a fluorescence mode at room temperature. Table 1 below lists coordination numbers (N) and Rh—O bond lengths obtained from the fitting of EXAFS data. Quantitative analysis revealed that there was no distinct Rh—Rh bonding in the 0.5 wt % Rh-ZSM-5 catalyst, indicating a single atom distribution of Rh species in the internal wall of zeolite. Furthermore, the coordination number of Rh—O bonding was between 3 and 4, suggesting that the isolated Rh cations were bonded with 3 to 4 oxygen atoms.

TABLE 1

Quantitative analyses of Rh-O and Rh-Rh contributions to EXAFS data

| Catalyst | Shell | N | R (Å) | $\sigma^2$ (Å²) |
|---|---|---|---|---|
| 0.5 wt % Rh-ZSM-5 | Rh-O | 3.6 ± 0.6 | 1.99 ± 0.03 | 0.007 |
| | Rh-Rh | 0 | — | — |

Using CO as a probe molecule, DRIFTS was performed on the active Rh-ZSM-5 catalysts at ambient conditions. Di-carbonyl species were formed on isolated Rh cations, whereas on Rh nanoparticles, single CO binds in both atop and bridged configuration. All three binding modes of CO were present in the samples of 1.0 wt % Rh-ZSM-5 and 0.5 wt % Rh-ZSM-5. Absorption peaks at 2116 cm$^{-1}$ and 2049 cm$^{-1}$ resulted from the symmetrical and asymmetrical stretching of CO of the isolated mononuclear $Rh^I(CO)_2$ species, while the peak at 2082 cm$^{-1}$ resulted from either the atop binding of CO on Rh nanoparticles or isolated $Rh^I(CO)_3$ species. See Matsubu et al., JACS, 2015, 137, 3076. A broad peak centered at 1885 cm$^{-1}$ was attributed to bridged binding of CO on Rh nanoparticles. Moreover, as to sample 0.5 wt % Rh-ZSM-5 washed (i.e., an additional washing step was applied to this sample before the reduction step to remove the Rh species on the external surface of zeolite), peaks at 2082 cm$^{-1}$ and 1885 cm$^{-1}$ were nearly absent, which indicates the preponderance of isolated dicarbonyl $Rh^I(CO)_2$ species. Thus, DRIFTS study unambiguously shows that isolated Rh species were the active site.

Example 2: Study of Direct Conversion of Methane to Oxygenates

Conversion of Methane to Oxygenates

A study was performed to assess the Rh-ZSM-5 catalyst prepared in Example 1 for converting methane to oxygenates in a Parr high-pressure reactor, which tolerates a maximal pressure of 2000 psi.

The Rh-ZSM-5 catalyst was added into 20 mL of deionized water, followed by ultrasonic sonication for 1 minute. A magnetic stir bar was used to continuously stir the solution during the reaction. A K-type thermocouple was attached to the Parr reactor to directly measure the temperature of the solution. The reactor vessel was pressurized with $O_2$ (0.5-4 bar), CO (5 bar), and $CH_4$ (20 bar); and then placed in an oil bath that was pre-heated to a desired temperature. Subsequently, the resulting solution was heated to a certain temperature, typically 150° C., for a certain amount of time (e.g., 1 h) with constant stirring. After the reaction, the reactor was removed from the oil bath and cooled down with ice. Once the solution temperature was below 10° C., a gas composition was analyzed using a mass spectrometer to check for $CO_2$ formation, and the liquid thus formed was collected in a vial after filtering all solid particles. The amount of $CO_2$ through direct CO oxidation was determined from a separate experiment using the identical reaction conditions but without $CH_4$. Thus the amount of $CO_2$ originated from $CH_4$ is calculated by the subtraction of $CO_2$ by CO oxidation from the total amount of $CO_2$ formed.

On the other hand, the amount of oxygenates in the liquid was quantified by Nuclear Magnetic Resonance (NMR) measurement. $^1H$ NMR spectra were measured on a Bruker AVANCE III 500 spectrometer. The measurement was calibrated by using a 1% tetramethylsilane (TMS)/$CDCl_3$ internal standard. A 0.6 mL liquid was mixed with 0.1 mL of $D_2O$ to make a solution in an NMR sample tube for the measurement. All $^1H$ NMR spectra were recorded using a pre-saturation solvent suppression technique to suppress the dominant $H_2O$ signal. See Grzesiek et al., *Journal of the American Chemical Societ,* 1993, 115, 12593. The identified oxygenates products were methanol ($\delta$=3.36 ppm), acetic acid ($\Delta$=2.08 ppm), and formic acid ($\Delta$=8.33 ppm). These products were quantified by comparing the $^1H$ NMR signal against calibration curves of each molecule.

A Comparative Study on Conversion of Methane to Oxygenates

A comparative study was conducted to assess the catalytic performance of the Rh-ZSM-5 catalyst on the conversion of methane to oxygenates under various conditions. Methane conversion on a 0.5 wt % Rh-ZSM-5 catalyst produced $CH_3OH$, HCOOH, $CH_3COOH$, and $CO_2$. The quantitative analyses of the yields of these products by using NMR (liquid oxygenates) and mass spectrometry (gases) is described in EXAMPLE 1.

Shown in Table 2 below are comparative yields of liquid oxygenates using pure ZSM-5 catalyst and 0.5 wt % Rh-ZSM-5 catalyst under various conditions.

to 150° C. for 1 hour. In row 5, an experiment was conducted, following the procedure set forth in the preceding paragraph in EXAMPLE 2 (see page 8, penultimate paragraph, supra), to unexpectedly generate significant amounts of oxygenates, i.e., methanol (1224 μmol/gcat), acetic acid (4957 μmol/gcat), and formic acid (7753 μmol/gcat).

The comparative data set forth above indicate that a method of this invention unexpectedly produces desired oxygenates, i.e., methanol and acetic acid, in high yield even under very mild conditions.

Example 3: Effects of Various Parameters on Direct Conversion of Methane to Oxygenates Studies were conducted to evaluate effects of four parameters, i.e., reaction temperature, oxygen pressure, reaction time, and metal content in catalyst, on direct conversion of methane to oxygenates as follows.

Evaluation of Reaction Temperature on Converting Methane to Oxygenates

A study was performed to evaluate the effect of reaction temperature on the yield of oxygenates using the 0.5 wt % Rh-ZSM-5 catalyst. The reaction of methane with 20 mg of the catalyst, 20 bar $CH_4$, 5 bar CO, and 4 bar $O_2$ took place for 1 hour at a temperature higher than 110° C. and lower than 200° C. The reaction was conducted following the procedure described in EXAMPLE 2 above. When the reaction temperature was increased from 130° C. to 150° C., the yields of oxygenates, i.e., formic acid (HCOOH), methanol ($CH_3OH$), and acetic acid ($CH_3COOH$), were significant increased from 336, 182, and 154 μmol/gcat to 7753, 1224, and 4957 μmol/gcat, respectively. On the other hand, yields of the three oxygenates were found to be 4873, 1748, and 3721 μmol/gcat, respectively, when the reaction temperature

TABLE 2

Yields of liquid oxygenates using pure ZSM-5 and 0.5 wt % Rh-ZSM-5 catalyst under various conditions

| Catalyst | Conditions | Oxygenates (μmol/gcat) | | |
|---|---|---|---|---|
| | | $CH_3OH$ | HCOOH | $CH_3COOH$ |
| ZSM-5 | $CH_4$ + $O_2$ + CO, 150° C., 1 h | 0 | 0 | 0 |
| 0.5 wt % Rh-ZSM-5 | $CH_4$ + CO, 150° C., 1 h | 0 | 0 | 0 |
| 0.5 wt % Rh-ZSM-5 | $CH_4$ + $O_2$, 150° C., 1 h | 0 | 0 | 0 |
| 0.5 wt % Rh-ZSM-5 | $CH_4$ + $O_2$, 150° C., 1 h; purge, adding CO, 150° C., 1 h | 0 | 0 | 23 |
| 0.5 wt % Rh-ZSM-5 | $CH_4$ + $O_2$ + CO, 150° C., 1 h | 1224 | 7753 | 4957 |

As shown in Table 2 above, row 1, a blank experiment was conducted with pure ZSM-5 using 20 bar $CH_4$, 5 bar CO, and 4 bar $O_2$ at 150° C. for 1 hour, showing that pure ZSM-5 was not active in the conversion of $CH_4$ to oxygenates. In row 2, an experiment was conducted with 0.5 wt % Rh-ZSM-5 catalyst using 20 bar $CH_4$ and 5 bar CO without $O_2$ at 150° C. for 1 hour, showing no activity in the conversion of $CH_4$ to oxygenates. Similarly, in row 3, an experiment was conducted with 0.5 wt % Rh-ZSM-5 catalyst using 20 bar $CH_4$ and 4 bar $O_2$ without CO at 150° C. for 1 hour, also showing no activity in the conversion of $CH_4$ to oxygenates. In row 4, an experiment was conducted to afford 23 μmol/gcat of acetic acid. This experiment was conducted with 0.5 wt % Rh-ZSM-5 catalyst in a reactor containing only 20 bar $CH_4$ and 4 bar $O_2$ first, and the reactor was then cooled down to <10° C. and purged with helium (He) several times, followed by adding 5 bar CO and heating was further increased to 170° C. A decrease of the total yield of the oxygenates is likely due to an over-oxidation of oxygenate to $CO_2$. Indeed, from 150° C. to 170° C., the yield of $CO_2$ originated from $CH_4$ increased from 5840 to 15661 μmol/gcat, which is consistent with the decrease of the total yield of the oxygenates.

The data set forth above indicate that the method for converting methane to oxygenates using a Rh-ZSM-5 catalyst provides the oxygenates in both high yield and high selectivity at a temperature of 150° C.

Evaluation of Oxygen Pressure on Converting Methane to Oxygenates

To reduce an over-oxidation, a study was performed to evaluate the effect of oxygen pressure on the yield of oxygenates using the 0.5 wt % Rh-ZSM-5 catalyst. The reaction of methane with 20 mg of the catalyst, 20 bar $CH_4$, 5 bar CO, and $O_2$ under a certain pressure took place for 1 hour at 150° C. The reaction was conducted following the procedure described in EXAMPLE 2 above. It was found that, when the oxygen pressure was reduced from 4 bar to 2 bar, undesired formic acid and $CO_2$ formation was dramatically suppressed from 7753 and 5840 μmol/gcat to 790 and 0 μmol/gcat, respectively. By contrast, the desired methanol and acetic acid were reduced by ~3 times only; namely, from 1224 and 4957 μmol/gcat to 412 and 1519 μmol/gcat, respectively. Thus, the selectivity to acetic acid was greatly enhanced by reducing the oxygen pressure.

Unexpectedly, when the reaction took place for 3 hours in the presence of 2 bar oxygen, the acetic acid yield was 5482 μmol/gcat with selectivity higher than 65% of the three oxygenates (yields for formic acid and methanol: 1670 and 701 μmol/gcat, respectively). Although higher selectivity toward acetic acid was achieved with 0.5 bar $O_2$, the yield of the acetic acid was found to be 234 μmol/gcat.

The data set forth above indicate that the method for converting methane to oxygenates using a Rh-ZSM-5 catalyst provides the oxygenates in both high yield and high selectivity at an oxygen pressure of 1-2 bar.

Evaluation of CO pressure on Converting Methane to Oxygenates

A study was performed to evaluate the effect of CO pressure on the yield of oxygenates using the 0.5 wt % Rh-ZSM-5 catalyst. The reaction of methane with 20 mg of the catalyst, 20 bar $CH_4$, 0.5 bar $O_2$, and under a certain pressure of CO took place for 1 hour at 150° C. The reaction was conducted following the procedure described in EXAMPLE 2 above. It was found that, when the CO pressure was reduced from 5 bar to 1 bar, the desired product acetic acid unexpectedly increased from 234 μmol/gcat to 807 μmol/gcat. Thus, the yield and selectivity to acetic acid was greatly enhanced by reducing the CO pressure from 5 bar to 1 bar, when using 0.5 bar $O_2$ as the oxidant.

Evaluation of Reaction Time on Converting Methane to Oxygenates

A study was performed to evaluate the effect of reaction time on the yield of oxygenates using the 0.5 wt % Rh-ZSM-5 catalyst. The reaction of methane with 20 mg of the catalyst, 20 bar $CH_4$, 5 bar CO, and 4 bar $O_2$ took place at 150° C. The reaction was conducted following the procedure described in EXAMPLE 2 above. Table 3 below shows that the product yield and the selectivity to liquid oxygenates as a function of reaction time (t). At t=0.25 h, the selectivity of liquid oxygenates was close to 90%, the yields of HCOOH, MeOH, and $CH_3COOH$ were 2227, 756, and 1233 μmol/gcat, respectively. At longer reaction time, the yield of $CH_3COOH$ continuously increased, whereas the selectivity of liquid oxygenates dropped to various extent. For example, at t=1 h, the yield of $CH_3COOH$ increased to 4957 μmol/gcat, whereas the selectivity of liquid oxygenates dropped to about 70%. Notably, at t=2 h, the yield of $CH_3COOH$ further increased to 6635 μmol/gcat, whereas the selectivity of liquid oxygenates dropped to about 45%, and $CO_2$ became the dominant oxidation product.

TABLE 3

Effect of reaction time on the yield of oxygenates

| Reaction Time (h) | Catalyst | Liquid Product (μmol/gcat) | | | $CO_2$ (μmol/gcat) |
| --- | --- | --- | --- | --- | --- |
| | | HCOOH | MeOH | $CH_3COOH$ | |
| 0.25 | 0.5 wt % Rh-ZSM-5 | 2227 | 756 | 1233 | 481 |
| 0.5 | 0.5 wt % Rh-ZSM-5 | 9263 | 1329 | 3185 | 1976 |

TABLE 3-continued

Effect of reaction time on the yield of oxygenates

| Reaction Time (h) | Catalyst | Liquid Product (μmol/gcat) | | | $CO_2$ (μmol/gcat) |
| --- | --- | --- | --- | --- | --- |
| | | HCOOH | MeOH | $CH_3COOH$ | |
| 1 | 0.5 wt % Rh-ZSM-5 | 7753 | 1224 | 4957 | 5840 |
| 2 | 0.5 wt % Rh-ZSM-5 | 5053 | 948 | 6635 | 14605 |

The data set forth above indicate that the method for converting methane to oxygenates using a Rh-ZSM-5 catalyst provides the oxygenates in both high yield and high selectivity at a reaction time of 0.5-1 hour.

Evaluation of Metal Content in Catalyst on Converting Methane to Oxygenates

A study was performed to evaluate the effect of the rhodium content in a Rh-ZSM-5 catalyst on the yield of oxygenates. The reaction of methane with 20 mg of the catalyst, 20 bar $CH_4$, 5 bar CO, and 4 bar $O_2$ took place at 150° C. for 1 hour. The reaction was conducted following the procedure described in EXAMPLE 2 above.

The yields of liquid oxygenates as a function of the Rh content, i.e., 0.1 wt %, 0.5 wt %, and 1.0 wt %, in the Rh-ZSM-5 catalyst were recorded. It was found that, among the three catalysts, 0.5 wt % Rh-ZSM-5 exhibited the best catalytic performance. More specifically, catalyst 0.1 wt % Rh-ZSM-5 provided oxygenates HCOOH, MeOH, and $CH_3COOH$ in yields of 702, about 300, and 432 μmol/gcat, respectively; most unexpectedly, catalyst 0.5 wt % Rh-ZSM-5 provided oxygenates HCOOH, MeOH, and $CH_3COOH$ in yields of 7753, 1224, and 4957 μmol/gcat, respectively; and catalyst 1.0 wt % Rh-ZSM-5 provided oxygenates HCOOH, MeOH, and $CH_3COOH$ in yields of 1626, 946, and 1212 μmol/gcat, respectively.

The data set forth above indicate that the method for converting methane to oxygenates provides the oxygenates in both high yield and high selectivity using a Rh-ZSM-5 catalyst that has a rhodium content of 0.5 wt % in the catalyst.

Example 4: Direct Conversion of Methane to Methanol Using a Metal Zeolite Catalyst A study was performed to evaluate direct conversion of methane to methanol using a transition metal ion loaded zeolite catalyst as follows.

Four catalysts, i.e., 1.3 wt % IrCu-ZSM-5, 1.3 wt % IrFe-ZSM-5, 1.06 wt % IrPd-ZSM-5, and 1.0 wt % Ir-ZSM-5, were used in this study as shown in Table 4 below. The reaction of methane with 30-40 mg of catalyst, 20 bar $CH_4$, 5 bar CO, and 4 bar $O_2$ was performed for 1 hour at various temperatures. The reaction was conducted following the procedure described in EXAMPLE 2 above.

Unexpectedly, the reaction using catalyst 1.3 wt % IrCu-ZSM-5 afforded methanol as the predominant liquid product without producing undesired formic acid.

The data set forth above indicate that the method for converting methane to methanol provides the methanol in high yield and excellent selectivity using IrCu-ZSM-5, a two-metal ion zeolite catalyst.

TABLE 4

Direct conversion of methane to methanol

| Catalyst | Metal Ratio | Reaction Temperature (° C.) | Liquid Product (μmol/gcat) | | |
|---|---|---|---|---|---|
| | | | HCOOH | MeOH | CH$_3$COOH |
| 1.3 wt % IrCu-ZSM-5 | Ir:Cu 1:1 | 110 | 0 | 148 | 0 |
| 1.3 wt % IrCu-ZSM-5 | Ir:Cu 1:1 | 130 | 0 | 330 | 0 |
| 1.3 wt % IrCu-ZSM-5 | Ir:Cu 1:1 | 150 | 0 | 606 | 55 |
| 1.3 wt % IrFe-ZSM-5 | Ir:Fe 1:1 | 150 | 74 | 296 | 41 |
| 1.06 wt % IrPd-ZSM-5 | Ir:Pd 10:1 | 170 | 1549 | 482 | 126 |
| 1.0 wt % Ir-ZSM-5 | — | 170 | 160 | 80 | 15 |

Example 5: Preparation of a Two-Metal Ion Zeolite Catalyst

Detailed Below is a Process for Preparing a Two-Metal Ion Zeolite Catalyst

An IrPd-ZSM-5 catalyst was prepared by a sequential impregnation method as follows.

Mono-metal catalyst 1.0 wt % Ir-ZSM-5 was prepared by incipient wetness impregnation of dehydrated NH$_4$-ZSM-5 using an aqueous solution of IrCl$_3$ and was dried in a vacuum oven at room temperature overnight. The dried Ir-ZSM-5 catalyst was further dehydrated at 80° C. under vacuum for 2 hours before impregnating with Pd. The impregnation of 0.06 wt % Pd into the Ir-ZSM-5 catalyst was conducted using an aqueous solution of Pd(NH$_3$)$_4$Cl$_2$, followed by drying in a vacuum oven at room temperature overnight. The dried material thus obtained was further reduced in 5% H$_2$ (balanced in He) at 550° C. for 3 hours to obtain a IrPd-ZSM-5 catalyst. The molar ratio of Ir to Pd in the IrPd-ZSM-5 catalyst was calculated to be 10:1.

It was observed that, a two-metal ion zeolite catalyst synthesized by co-impregnation of Ir and Pd, or synthesized by impregnation of Ir into an palladium zeolite catalyst, showed much less activity.

In addition, an IrCu-ZSM-5 catalyst was prepared following the procedure described above with certain modifications. More specifically, catalyst 0.3 wt % Cu-ZSM-5 was synthesized by incipient wetness impregnation of dehydrated NH$_4$-ZSM-5 using an aqueous solution of Cu(NO$_3$)$_2$, followed by drying in a vacuum oven at room temperature overnight and calcination in air at 550° C. for 3 hours. Subsequently, 1.0 wt % Ir was impregnated to the Cu-ZSM-5 catalyst using an aqueous solution of IrCl$_3$, followed by drying in a vacuum oven at room temperature overnight. The material thus obtained was further reduced in 5% H$_2$ (balanced in He) at 550° C. for 3 hours to obtain an IrCu-ZSM-5 catalyst. The molar ratio of Ir to Cu in the IrCu-ZSM-5 catalyst was calculated to be 1:1.

By contrast, an IrCu-ZSM-5 catalyst synthesized by impregnation of Cu into an iridium zeolite catalyst, or synthesized without the calcination in air at 550° C., showed much lower activity.

Example 6: Preparation and Evaluation of a Three-Metal Ion Zeolite Catalyst

A PdCuIrZSM-5 (1.36 wt %) catalyst was prepared by a sequential impregnation method as follows.

0.3 wt % CuZSM-5 was synthesized by incipient wetness impregnation of dehydrated NH$_4$-ZSM-5 with an aqueous solution of Cu(NO$_3$)$_2$, followed by drying in a vacuum oven at room temperature overnight and calcination in air at 550° C. for 3 hours. 1 wt % Ir was impregnated to the Cu-ZSM-5 using an IrCl$_3$ solution and then the material thus obtained was dried in a vacuum oven at room temperature overnight. The dried material was further dehydrated at 80° C. under vacuum for 2 hours and then 0.06 wt % Pd was impregnated through an aqueous solution of Pd(NH$_3$)$_4$Cl$_2$, followed by drying in a vacuum oven at room temperature overnight. The product was reduced in 5% H$_2$ at 550° C. for 3 hours to provide the 1.36 wt % PdCuIrZSM-5 catalyst. The atomic ratio of Pd:Cu:Ir was found to be 1:10:10.

Catalytic activity of 1.36 wt % IrCuPd/ZSM-5 (Ir:Cu: Pd=10:10:1) was studied at different reaction times under the following conditions: 4 bar O$_2$, 5 bar CO, 20 bar CH$_4$, 40 mg catalyst, 150° C., and 20 mL H$_2$O.

It was observed that the trimetallic catalyst PdCuIrZSM-5 unexpectedly exhibited better catalytic performance than bimetallic catalysts PdIrZSM-5 and CuIrZSM-5. More specifically, at 1-hour reaction time, the methanol yield using 1.36 wt % PdCuIrZSM-5 catalyst was 1188 μmol/gcat, while the methanol yield using 1.3 wt % CuIrZSM-5 under the same conditions was only 606 μmol/gcat; and at 3-hour reaction time, the methanol yield using 1.36 wt % PdCuIrZSM-5 catalyst was 1600 μmol/gcat with methanol selectivity of 56% based on the total (liquid plus gaseous) carbon products.

Example 7: Preparation and Evaluation of a Rhodium Catalyst Loaded on TiO$_2$

A Rh-TiO$_2$ catalyst was prepared by a deposition-precipitation method as follows.

A commercial titanium oxide or titania, TiO$_2$ (Millenium, G5), was used to prepare a dispersed Rh catalyst. Rhodium species were deposited onto TiO$_2$ via a standard deposition-precipitation method, using an aqueous solution of Rh(NO$_3$)$_3$. A fixed amount of Rh(NO$_3$)$_3$ solution was added drop-wise into the TiO$_2$ suspension. The resulting mixture was maintained at a temperature of 80° C. and pH of 8.5 to form solids. Subsequently, the solids were filtered, and transferred to an ethanol solution to form slurry, which was exposed to UV irradiation with an 8 W BL lamp centered at 265 nm. During the irradiation, rhodium cations were anchored on certain surface sites of the titania, while weakly bound excess rhodium species were readily removed by hydrochloric acid leaching. Use of 2.5 wt % Rh/TiO$_2$ under UV irradiation for 3 hours anchored 0.65 wt % rhodium as single atoms.

The Rh/TiO$_2$ material thus obtained was used to catalyze the oxidation of methane in aqueous phase and, unexpectedly, selective formation of methanol without forming any formic acid or acetic acid was observed. See Table 5 below.

Shown in Table 5 are catalytic activities of catalysts RhZSM-5, Rh/TiO$_2$, and RhNaZSM-5 in oxidation of methane.

TABLE 5

Catalytic activity of different Rh catalysts

| | HCOOH | CH$_3$OH | CH$_3$COOH | CO$_2$ |
|---|---|---|---|---|
| 0.5 wt % RhZSM-5 | 1670 | 701 | 5482 | 574 |
| 0.65 wt % Rh/TiO$_2$ | 0 | 231 | 0 | not detected |
| 0.5 wt % RhNaZSM-5 | 289 | 430 | 57 | not detected |

Conditions: 20 mg catalyst, 2 bar O$_2$, 5 bar CO, 20 bar CH$_4$, 150° C., 3 hour-test.

This study demonstrates that porous metal oxide supports, e.g., $TiO_2$ (a porous metal oxide support with very different pore structure and acidity compared with zeolites), were able to anchor Rh cations and form an active catalyst. Other cations, e.g., Au, Pt, Pd, Cu, Fe, Zn, and Ir, could also be prepared on $TiO_2$ surfaces to form active and selective catalysts.

Further, this study also shows that Brønsted acid sites of the zeolite were necessary only for the formation of acetic acid, while rhodium cations could catalyze the oxidation of methane to methanol exclusively when a metal oxide support, e.g., titania, that did not contain the Brønsted acid sites was used. This was also supported by the test using 0.5 wt % RhNaZSM-5 catalyst, in which the Brønsted acid sites were exchanged by Na ions from an aqueous solution of a sodium salt. It was observed that the acetic acid production was significantly suppressed when Brønsted acid sites were largely removed by using RhNaZSM-5 catalyst. Over oxidation to $CO_2$ was also greatly suppressed.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

Further, from the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A method of converting methane to an oxygenate, the method comprising:
   providing a transition metal ion loaded zeolite catalyst,
   converting methane to an oxygenate with the transition metal ion loaded zeolite catalyst in an aqueous medium in the presence of gaseous $O_2$ and CO at a temperature lower than 200° C., and
   collecting the oxygenate thus formed,
   wherein the transition metal ion loaded zeolite catalyst is a rhodium zeolite catalyst, a copper zeolite catalyst, an iron zeolite catalyst, a nickel zeolite catalyst, an iridium zeolite catalyst, or a combination thereof; and the oxygenate, in liquid form, contains both methanol and acetic acid, in which the content of the methanol, the acetic acid, or both the methanol and the acetic acid combined is greater than 50 mol %.

2. The method of claim 1, wherein the transition metal ion loaded zeolite catalyst is a rhodium zeolite catalyst.

3. The method of claim 2, wherein the rhodium zeolite catalyst is a Rh-ZSM-5 or Rh-MOR catalyst.

4. The method of claim 3, wherein the Rh-ZSM-5 or Rh-MOR catalyst is prepared by incipient wetness impregnation of a rhodium nitrate solution into $NH_4$-ZSM-5 or $NH_4$-MOR.

5. The method of claim 3, wherein the Rh-ZSM-5 or Rh-MOR catalyst has a Rh loading of 0.1-1.0 wt %.

6. The method of claim 2, wherein the rhodium zeolite catalyst is a Rh-ZSM-5 catalyst and the Rh-ZSM-5 catalyst is further treated in 5% $H_2$/He at 550° C.

7. The method of claim 2, wherein the rhodium zeolite catalyst is a Rh-ZSM-5 catalyst and the Rh-ZSM-5 catalyst is prepared from a zeolite having a Si/Al ratio of 15.

8. The method of claim 5, wherein the Rh-ZSM-5 or Rh-MOR catalyst has a Rh loading of 0.5 wt %.

9. The method of claim 1, wherein the transition metal ion loaded zeolite catalyst is IrCuPd-ZSM-5 or RhNa-ZSM-5.

10. The method of claim 1, wherein the transition metal ion loaded zeolite catalyst has a transition metal loading of 0.1-1.0 wt %.

11. A method of converting methane to methanol, the method comprising:
    providing a transition metal ion loaded catalyst,
    converting methane to methanol with the transition metal ion loaded catalyst in an aqueous medium in the presence of $O_2$ and CO at a temperature lower than 200° C., and
    collecting the methanol thus formed,
    wherein the transition metal ion loaded catalyst is a transition metal catalyst loaded on a titanium oxide ($TiO_2$) support or a transition metal zeolite catalyst selected from the group consisting of a rhodium zeolite catalyst, a copper zeolite catalyst, an iron zeolite catalyst, a nickel zeolite catalyst, an iridium zeolite catalyst, and a two-metal ion zeolite catalyst.

12. The method of claim 11, wherein the transition metal ion loaded catalyst is a rhodium catalyst loaded on a $TiO_2$ support.

13. The method of claim 11, wherein the transition metal ion loaded catalyst is a copper zeolite catalyst or an iron zeolite catalyst.

14. The method of claim 11, wherein the transition metal ion loaded catalyst is a two-metal ion zeolite catalyst.

15. The method of claim 13, wherein the copper zeolite catalyst or the iron zeolite catalyst has a copper or iron loading of 0.1-1.0 wt %.

16. The method of claim 14, wherein the two-metal ion zeolite catalyst contains two transition metals selected from the group consisting of Pd and Ir, Cu and Ir, and Fe and Ir.

17. The method of claim 14, wherein the two-metal ion zeolite catalyst contains two transition metals selected from the group consisting of Pd and Rh, Cu and Rh, and Ag and Rh.

18. The method of claim 16, wherein the two-metal ion zeolite catalyst has a Pd, Cu, Fe, or Ir loading of 0.1-1.0 wt %.

19. The method of claim 16, wherein the two transition metals are Cu and Ir, or Fe and Ir.

20. The method of claim 19, wherein the two-metal ion zeolite catalyst has a Cu, Fe, or Ir loading of 0.1-1.0 wt %, and a Cu/Ir or Fe/Ir molar ratio of 1:1.

21. A two-metal ion zeolite catalyst for converting methane to methanol, the catalyst comprising two transition metals selected from the group consisting of Pd and Ir, Cu and Ir, Fe and Ir, and Pd and Rh.

22. A method of preparing the two-metal ion zeolite catalyst of claim 21, the method comprising:
    forming a transition metal ion loaded zeolite catalyst, the catalyst containing a first transition metal,
    introducing a second transition metal into the catalyst thus formed to obtain a two-metal ion zeolite catalyst, and
    reducing the two-metal ion zeolite catalyst thus obtained in 5% $H_2$/He, wherein the two-metal ion zeolite catalyst contains two transition metals selected from the group consisting of Pd and Ir, Cu and Ir, Fe and Ir, and Pd and Rh.

* * * * *